United States Patent [19]

Grandiere

[11] Patent Number: 4,790,643

[45] Date of Patent: Dec. 13, 1988

[54] APPARATUS FOR DETECTING AND TREATING TROUBLES WITH BINOCULAR VISION

[75] Inventor: Brigitte Grandiere, Evreux, France

[73] Assignee: Briot International, Pont De L'Arche, France

[21] Appl. No.: 24,077

[22] Filed: Mar. 10, 1987

[51] Int. Cl.$^4$ ............................................. G02C 7/16
[52] U.S. Cl. ...................................... 351/45; 351/200; 351/201
[58] Field of Search ................... 351/200, 201, 45, 46, 351/47

[56] References Cited

U.S. PATENT DOCUMENTS

| 505,000 | 9/1983 | Price | 351/46 |
|---|---|---|---|
| 3,492,989 | 3/1970 | Allen | |
| 3,819,189 | 6/1974 | Goode | 351/45 |
| 4,522,474 | 11/1985 | Slavin | |

FOREIGN PATENT DOCUMENTS 2489136  5/1982  France .

Primary Examiner—Rodney B. Bovernick
Assistant Examiner—P. M. Dzierzynski
Attorney, Agent, or Firm—Gerald J. Ferguson, Jr.

[57] ABSTRACT

A frame (1) includes means (3) for being held in front of the eyes, and means (6) for supporting and guiding the displacement of a moving opaque element (7) such as shutter movable between a central position in which it leaves binocular vision free, and two opposite side positions preventing vision via one or other of the eyes when the head is tilted.

10 Claims, 2 Drawing Sheets

APPARATUS FOR DETECTING AND TREATING TROUBLES WITH BINOCULAR VISION

The invention relates to apparatus for facilitating the detection of and for assisting in the treatment of troubles with binocular vision, and in particular in very young children. Examples of such troubles include strabism (i.e. squinting) and amblyopia (e.g. the "lazy eye" side effect common in cases of squinting). Such vision is corrected by medical, orthoptic, or surgical treatment. Orthoptic treatment consists in re-establishing good monocular visual acuity and, if possible, in developing binocular vision by making the eyes of the patient work in alternation, separately and then simultaneously.

The earlier that orthoptic treatment is begun, the better the results, and the treatment may advantageously be applied to babies in the first months of life. Unfortunately, equipment for orthoptic and ophthalmologic investigation of babies and very young children is practically non-existent.

BACKGROUND OF THE INVENTION

Spectacle frames exist which are fitted with glass containing liquid crystals. By suitable electronic polarization, such glass can be made opaque or transparent, and can be made to alternate between being opaque and transparent at any desired rate and independently for each eye. Such spectacles can be used for detecting, diagnosing, and treating some anomalies in vision, in particular strabism.

Such high-performance equipment is complex, expensive, and not very suitable for very young children.

Preferred embodiments of the present invention provide apparatus which is simple, very cheap, does not require electronic circuits, and which can be used with very young children even when only a few months' old, for early and reliable detection of troubles with vision, and also for providing effective treatment thereof.

SUMMARY OF THE INVENTION

The present invention provides apparatus for detecting and treating troubles with binocular vision, the apparatus comprising a frame for use in front of the eyes and means for holding said frame in such an in-use position, said frame being transparent at least in those regions thereof intended to be placed directly in front of the eyes, and the apparatus including the improvement whereby said frame includes at least one moving opaque element together with support and guide means fixed to the frame for supporting said at least one moving opaque element and for guiding movement thereof relative to said frame between at least two positions: a first position in which said opaque element allows free binocular vision; and a second position in which it prevents vision with one or other of the eyes.

The moving opaque element may be moved by any suitable means, and preferably in accordance with the invention it is moved under the effect of gravity.

The frame has an elongate body which preferably includes a hollow volume, and more advantageously still an internal hollow volume contained in the thickness thereof, with the moving opaque element being movably mounted in said hollow volume, preferably together with said support and guide means.

In one embodiment of the invention, the moving opaque element is a shutter mounted to pivot or to slide. In a variant, the body of the frame may be fitted with two shutters, each capable of occupying two different positions relative to respective eyes in order to block or unblock vision from said eyes.

In another embodiment, when the body of the frame includes an internal hollow volume, the volume is delimited by a concave bottom surface, i.e. a surface whose concave side is upwardly directed, and the moving opaque element is a body suitable for rolling over said concave surface.

In yet another embodiment, likewise including a frame having an internal hollow volume, the moving opaque element is an opaque liquid which partially fills said hollow volume.

BRIEF DESCRIPTION OF THE DRAWINGS

Embodiments of the invention are described, by way of example, with reference to the accompanying drawings, in which.

MORE DETAILED DESCRIPTION

Apparatus in accordance with the invention comprises a frame 1 made of material which is transparent, either totally transparent, or transparent at least in those regions which are located in front of the eyes when the frame is in use. The frame 1 is worn on the face like a spectacle frame, with a curved notch 2 in its bottom edge 1A for resting on the nose and with means for retaining it in this position, such as two side-pieces 3 which are preferably foldable (see FIG. 1), or such as two tapes 4 (see FIG. 10) which are tied together at the back of the head, or any other suitablee means. These means have been omitted from FIGS. 2 to 11.

Figure 1:
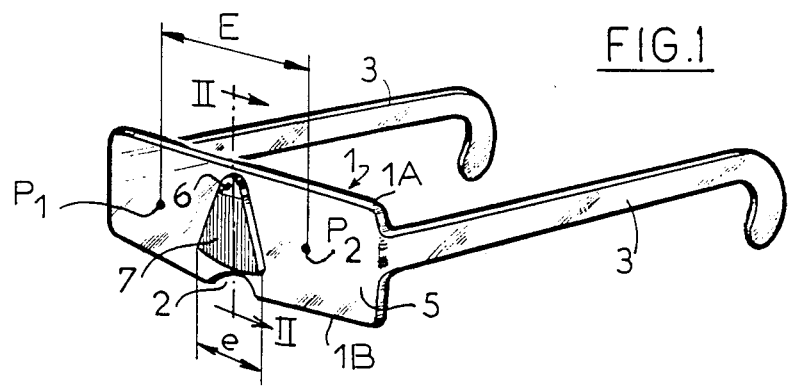
FIG. 1 is a perspective overall view of apparatus in accordance with the invention and including a pivoting shutter.
Figure 2:
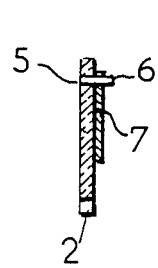
FIG. 2 is a section on line II—II of FIG. 1.

In the example shown in FIGS. 1 and 2, the frame 1 comprises a body 5 made entirely of transparent material such as methyl methacrylate. The body is elongate in shape so as to extend in front of both eyes when in use, and it carries a pivot 6 which extends perpendicularly forwardly therefrom, i.e. away from the face. The pivot 6 is close to the top edge 1B of the elongate body 5 and it is situated in the middle thereof so as to lie in the plane of symmetry of the face between the eyes when the apparatus is in use. A shutter 7 is suspended from the pivot 6 and is in the form of a circular sector centered on the pivot 6 and free to swing from side to side as the user tilts the head.

In the figures, the pupils of a user's eyes are symbolized by points P1 and P2. The inter-pupil spacing is a distance E marked in FIG. 1. The width of the wide end of the shutter 7 is e, where e is equal to about one-half of the inter-pupil spacing E. When the user tilts the head, the shutter 7 is subjected to the effect of gravity. Its rest position relative to the frame changes and it lies in front of the pupil P1 or the pupil P2, thereby blocking vision from the corresponding eye.

Figures 3, 4:
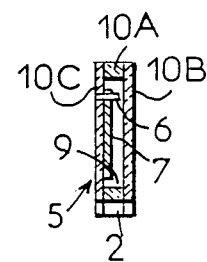
FIGS. 3 and 4 are section views similar to FIG. 2, showing variant embodiments of apparatus in accordance with the invention.

FIG. 2 shows the pivoting shutter 7 suspended immediately in front of the body 5. However, it is preferable to protect the shutter by housing it in a hollow volume 8 hollowed out in the thickness of the body 5, as can be seen in FIG. 3. It is even more advantageous for the hollow volume to be a fully enclosed or internal volume 9 included in the thickness of the body 5, as shown in FIG. 4. In this case, the body 5 comprieses a first or middle plate 10A having a hole therethrough which becomes the internal volume 9 when solid front and back plates 10B and 10C are fixed thereto using an adhesive or by welding. The middle plate 10A may be made of opaque material, and the height and the length of the internal volume 9 should be such as to allow full vision by both eyes when the user holds the head upright, with the shutter then occupying the position shown in FIG. 1.

In the examples shown in FIGS. 5 to 8, the body 5 includes an internal volume 9 as described above. In the example shown in FIGS. 5 and 6 this internal volume 9 is delimited by a bottom surface 11 which is concave, i.e. the concave side of said surface faces upwards when the apparatus is in use, and the moving opaque element is an element 12 suitable for rolling on the concave surface 11, e.g. a disk of opaque material which is loosely contained in the internal volume 9. In a position of normal binocular vision, the element 12 occupies the lowest point of the concave surface 11, which point lies in the plane of symmetry of the face. When the head is tilted (FIG. 6) the opaque element 12 moves to a position in front of one or other of the pupils (in this case P1). The dimensions of the inside volume 9 and of the rolling opaque element 12 are established to this end.

Figure 7:
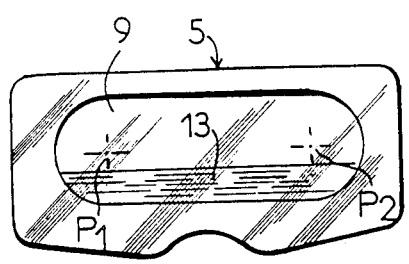
FIGS. 7 and 8 are front views of apparatus in accordance with the invention using an opaque liquid and shown in two different positions of use.
Figure 8:
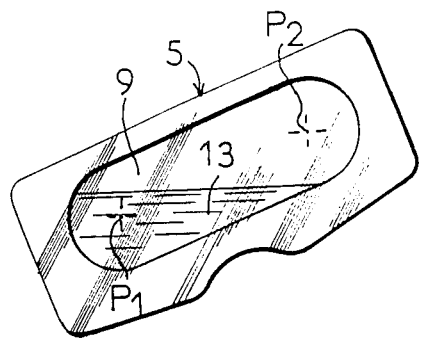

In the example shown in FIGS. 7 and 8, the internal volume 9 contains an opaque liquid 13. In the binocular vision position, this liquid 13 extends over the bottom of the volume 9 and does not block vision (see FIG. 7). When the head is tilted, the liquid 13 collects in one or other end of the internal volume 9 and blocks the view of the corresponding eye.

It is also possible to use two immiscible liquids, one denser than the other, and completely filling the internal volume 9. Similarly, in the example shown in FIGS. 5 and 6, the volume 9 could completely filled with a transparent liquid in which the rolling element 12 is immersed. As a result the movements of the opaque liquid or of the rolling member are somewhat braked, and take place more slowly and more smoothly.

Figure 9:
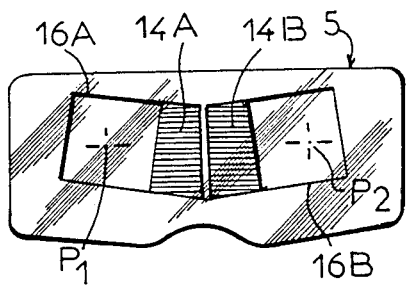
FIGS. 9 and 10 are views similar to FIG. 5 showing two different variants of apparatus in accordance with the invention using sliding shutters, with FIG. 9 showing a gravity-return variant, and FIG. 10 showing a spring-return variant.

In the example shown in FIG. 9, the apparatus includes two moving opaque elements 14A and 14B which are independent of each other and which are disposed on either side of a center stop 15 located, when in use, in the plane of symmetry of the face. Each moving element 14A and 14B is supported and guided by suitable means such as corresponding pairs of of slideways 16A and 16B extending in opposite directions from the center stop 15. These slideways 16A and 16B may project from the face of the body 5. In a variant, they may be constituted by the top and bottom faces 9A and 9B respectively of the internal volume 9. The shutters 14A and 14B slide longitudinally relative to the frame 1 between two positions: a position in which they are both in abutment against the center stop 15, thereby allowing binocular vision; and a position in which one of the shutters has slid to the opposite end of its slideways, thereby blocking vision from the corresponding pupil. In order to ensure that each of the shutters 14A and 14B tends to return towards the center stop 15 under the effect of gravity, the slideways 16A and 16B slope slightly downwardly towards the center stop 15 as shown in FIG. 9.

Figure 10:
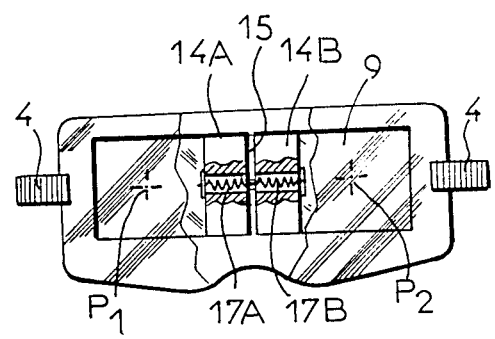

FIG. 10 relates to a variant embodiment in which the sliding shutters 14A and 14B are supported and guided in translation in an internal volume 9 whose top and bottom surfaces constitute the slideways 16A and 16B. These slideways are rectilinear and in line with each other for each eye. In the binocular vision position the slideways are horizontal. Each sliding shutter 14A, 14B moves away from the center stop 15 when the apparatus is tilted by sliding under the effect of gravity against the action of a corresponding return spring 17A or 17B which is connected to the center stop 15 and which urges the shutter back towards said center stop.

Figure 11:
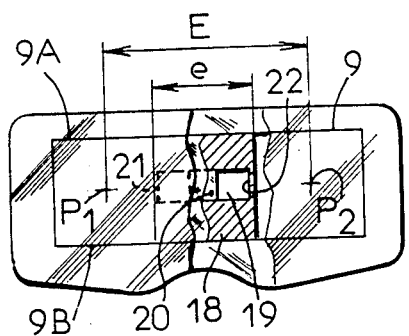
FIG. 11 is a front view showing a sliding shutter.

FIG. 11 shows another variant including a single rectangular sliding shutter 18 having a rectilinear groove 19 in one of its main faces, with said groove retaining a guide peg 20. The guide peg 20 projects into the middle of the internal volume 9 in the body 5. The stroke of the sliding shutter 18 is limited by end stops 21 and 22 provided at the ends of the groove 19. The length of the shutter 18 is e, where e is equal to half of the inter-pupil distance E.

In the FIG. 11 example, the shutter 18 is guided internally by the guide and support peg 20. It could be guided and supported externally by the top and bottom faces 9A and 9B of the internal volume 9, in which case the guide peg 20 could be omitted.

Returning to FIG. 2, it can be seen that the body 5 could be made of transparent material with the guide peg 20 projecting from one of its main faces and with the sliding shutter 18 being carried and guided on said peg, in which case the peg and the groove 19 should have complementary T-shaped profiles.

Figure 5:
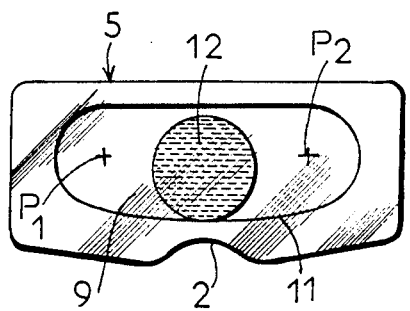
FIGS. 5 and 6 are front views showing apparatus in accordance with the invention including a rolling opaque element shown in two different positions of use.
Figure 6:
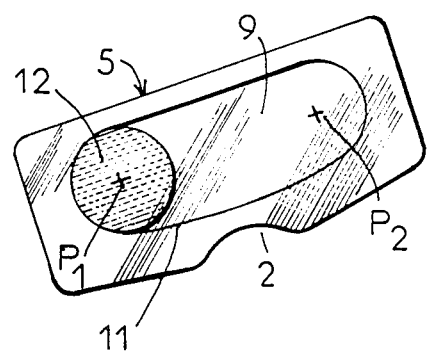
Figure 12:
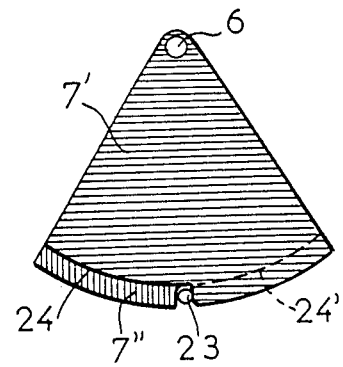
FIG. 12 is a detail showing a pair of pivoting shutters mounted one behind the other.

The examples shown in FIGS. 1,5, and 11 could be fitted with pairs of moving opaque elements such as the pivoting shutter 7 or the rolling element 12 or the sliding shutter 18 with the two elements being disposed one on front of the other in the binocular vision position. Each of these elements would then move solely between two positions (as is the case for the shutters of FIGS. 9 and 10) relative to a common center stop 23 such as that shown in FIG. 12 for a pair of pivoting shutters 7' and 7'', each of which has a stepped bottom edge enabling it to move in one direction only.

The apparatus in accordance with the invention can be used to detect certain troubles with vision in babies and very small children merely by observing their behaviour, and without requiring a third person to perform any king of maneuver or manipulation.

When a child is suffering from trouble with binocular vision, the child tends to tilt the head in such a way as to obtain monocular vision. The moving opaque element then covers the defective eye.

For treating such troubles, the moving opaque element moves to left and to right depending on the child's head movements, thereby providing alternating monocular vision. The apparatus thus helps avoid the development of amblyopia.

Further, by virtue of the way in which a child's vision alternates with movement of the head encourages central fixation of view, thus helping the development of binocular vision with the head in an upright position.

I claim:

1. Apparatus for detecting and treating troubles with binocular vision especially of a baby, the apparatus comprising a frame for use in front of the eyes of the baby and means for holding said frame in such an in-use position, said frame being transparent at least in those regions thereof intended to be placed directly in front of the center of the eyes' pupils, and the apparatus including at least one moving opaque element wherein support and guide means are fixed to the frame for supporting said at least one movable opaque element and for guiding reversible movement thereof relative to said frame under the effect of gravity between three position: a first position in which said opaque element uncovers the both pupil centers; and second and third positions in which it prevents vision with respectively the one or other of the eyes, by covering the corresponding pupil center, depending on the tilting of the head of the baby and wherein the movavle element is dimensioned so that it is not obstructed by the nose of the baby when moved between the said three positions.

2. Apparatus according to claim 1, including two opaque movable elements, each displaceable between two positions: i.e. respective first positions in which binocular vision is left free; and respective second positions in which vision using a corresponding one of the eyes is prevented.

3. Apparatus according to claim 2, wherein said two opaque elements are disposed symmetrically on either side of a center stop on said frame, said center stop being located in the plane of symmetry of the face when the apparatus is in use.

4. Apparatus according to claim 2, wherein said two movable opaque elements are disposed one in front of the other in their respective first positions allowing free binocular vision, with at least one stop limiting movement of each element in respective opposite directions.

5. Apparatus according to claim 1, wherein the frame includes an elongate body having a hollow volume in which said movable element is mounted by said support and guide means.

6. Apparatus according to claim 5, wherein said hollow volume is an internal volume included in the thickness of the frame.

7. Apparatus according to claim 6, wherein the movable opaque element is suitable for rolling and is included within said internal volume, said internal volume being delimited in part, by a bottom surface having a concave face which is upwardly directed when the apparatus is in use, with the lowest point of said concave surface being substantially equidistant between the eyes, said opaque element being supported and guided by said surface and being capable of rolling freely under the effect of gravity.

8. Apparatus according to claim 6, wherein the movable opaque element is a liquid enclosed in the internal volume, and having a free level beneath the pupil centers when the wearer's head stands upright.

9. Apparatus according to claim 1, wherein the movable opaque element is a shutter mounted to pivot under the effect of gravity about an upper pivot extending perpendicularly to the frame at a point situated substantially in the plane of symmetry of the face when the apparatus is in use.

10. Apparatus according to claim 1, wherein the movable opaque element is a shutter mounted to slide relative to the frame, on a limited transverse distance centered on the plane of symmetry of the wearer's face.

* * * * *